United States Patent [19]
Ackley et al.

[11] Patent Number: 6,103,467
[45] Date of Patent: Aug. 15, 2000

[54] METHOD AND SYSTEM FOR SYNTHESIZING OLIGONUCLEOTIDES USING NUCLEOTIDE-SPECIFIC DISPENSING BARS

[75] Inventors: Donald E Ackley, Lambertville, N.J.; Chan-Long Shieh, Paradise Valley; Thomas B. Harvey, III, Scottsdale, both of Ariz.

[73] Assignee: Motorola, Inc., Schaumburg, Ill.

[21] Appl. No.: 08/901,102

[22] Filed: Jul. 28, 1997

Related U.S. Application Data

[62] Division of application No. 08/643,082, Apr. 17, 1996, Pat. No. 5,733,509.

[51] Int. Cl.[7] .................................................. C08F 2/00
[52] U.S. Cl. ............................................. 435/6; 435/283.1
[58] Field of Search ...................................... 435/6, 283.1

[56] References Cited

U.S. PATENT DOCUMENTS 5,429,807  7/1995  Matson et al. .......................... 422/131

*Primary Examiner*—Scott W. Houtteman
*Attorney, Agent, or Firm*—James E. Gauger

[57] ABSTRACT

A plurality of oligonucleotides are synthesized at a plurality of locations on a substrate using a plurality of dispensing bars. Each of the plurality of dispensing bars has a respective plurality of dispensing heads arranged along a respective axis. Each of the plurality of dispensing bars is operative to selectively deposit a volume of a respective one of a plurality of nucleotide bases in any of a row of locations. A positioning mechanism positions the substrate with respect to the plurality of dispensing bars. A controller controls the plurality of dispensing bars and the positioning mechanism so that, at each of the plurality of locations, a respective sequence of nucleotide bases is deposited to form a respective oligonucleotide.

32 Claims, 4 Drawing Sheets

6,103,467

METHOD AND SYSTEM FOR SYNTHESIZING OLIGONUCLEOTIDES USING NUCLEOTIDE-SPECIFIC DISPENSING BARS

This application is a divisional of Ser. No. 08/643,082, filed Apr. 17, 1996, now U.S. Pat. No. 5,733,509.

FIELD OF THE INVENTION

The present invention relates to methods and systems for synthesizing an array of oligonucleotides probes on a substrate.

BACKGROUND OF THE INVENTION

Recently, an increased effort has been directed toward the development of chips for molecular detection. In general, a molecular detection chip includes a substrate on which an array of binding sites is arranged. Each binding site (or hybridization site) has a respective molecular receptor which binds or hybridizes with a molecule having a predetermined structure. A sample solution is applied to the molecular detection chip, and molecules in the sample bind or hybridize at one or more of the binding sites. The particular binding sites at which hybridization occurs are detected, and one or more molecular structures within the sample are subsequently deduced.

Of great interest are molecular detection chips for gene sequencing. These chips, often referred to as DNA chips, utilize an array of selective binding sites each having respective single-stranded DNA probes. A sample of single-stranded DNA fragments, referred to as target DNA, is applied to the DNA chip. The DNA fragments attach to one or more of the DNA probes by a hybridization process. By detecting which DNA probes have a DNA fragment hybridized thereto, a sequence of nucleotide bases within the DNA fragment can be determined.

A number of approaches have been devised for putting an array of molecular receptors on a substrate. Affymax has proposed a lithographic technique of synthesizing peptides or nucleic acids on a glass surface. To synthesize an array of n-mer oligonucleotide probes, 4 n lithographic write steps are required. This results from the four different constituent nucleotide bases (adenine, cytosine, guanine, and thymine) which can be located at each of the n nucleotide locations in an n-mer probe. A shortcoming of the lithographic technique is that a new set of lithographic masks must be produced if a new configuration of probes is desired in the array.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DETAILED DESCRIPTION OF A PREFERRED EMBODIMENT

Embodiments of the present invention advantageously provide a scalable and programmable approach to synthesizing oligonucleotide probes directly onto a diagnostic chip. A plurality of dispensing bars, each for a respective nucleotide, are utilized to sequentially deposit nucleotides on a substrate to form the oligonucleotides. As a result, a reduced number of write steps are required to synthesize the oligonucleotides in comparison to lithographic techniques. Further, an inexpensive approach is provided to fabricate disposable chips with a large number of probe sites.

Figure 1:
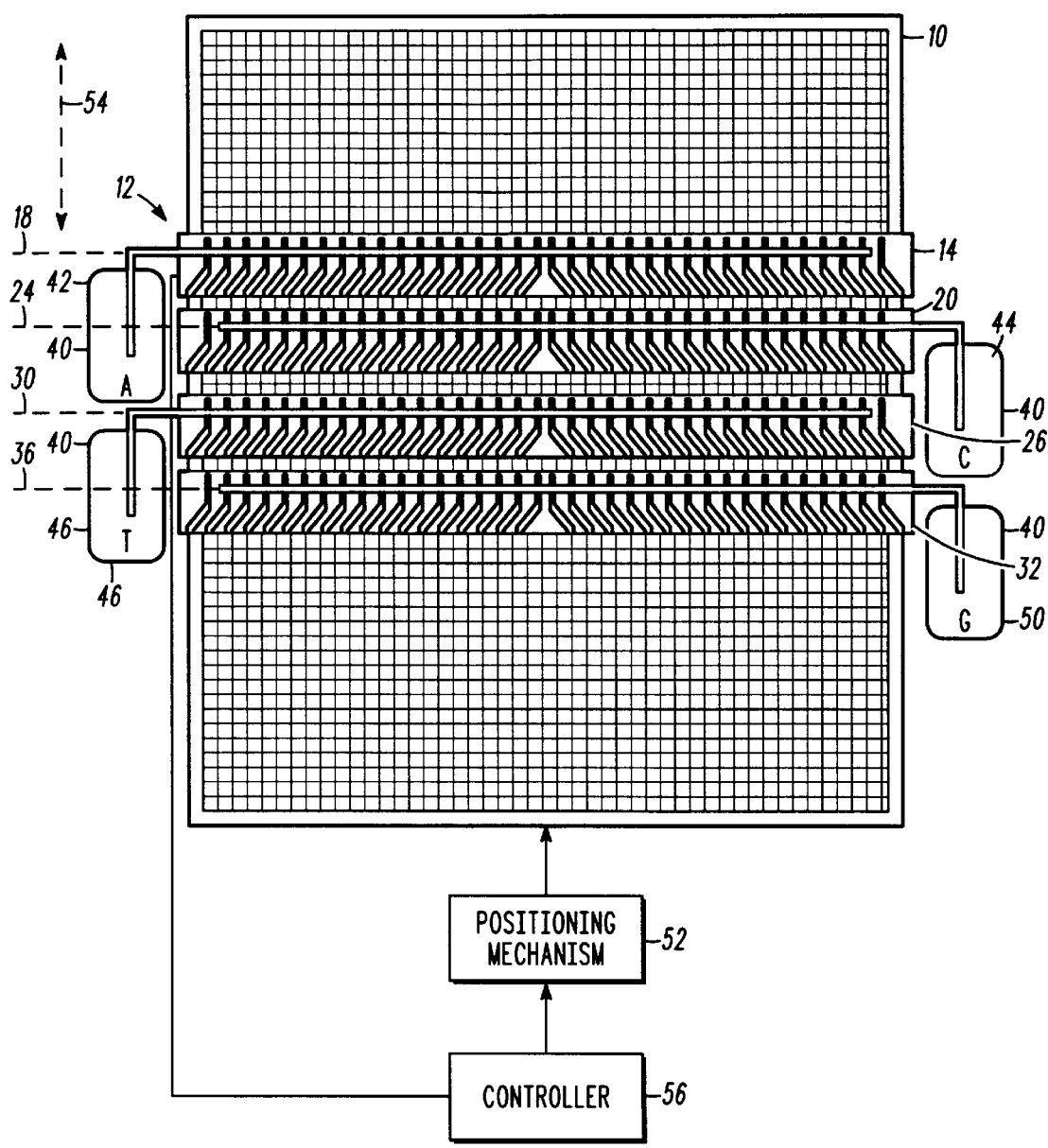
FIG. 1 is an illustration of an embodiment of a system for synthesizing a plurality of oligonucleotides at a plurality of locations on a substrate.

FIG. 1 is an illustration of an embodiment of a system for synthesizing a plurality of oligonucleotides at a plurality of locations on a substrate 10. The substrate 10 can be formed of materials which include, but are not limited to, silicon, paper, glass, and plastic. The substrate 10 can be either flexible or rigid, and can have any shape, including but not limited to a planar shape and a roll shape.

The plurality of locations are arranged as a plurality of rows on the substrate 10. The plurality of locations can be selective binding sites, for example, on a substrate which forms a gene sequencing chip or a disease diagnosis chip. Here, the system can be utilized to synthesize single-stranded DNA fragments directly onto the selective binding sites of the chip.

The system includes a plurality of dispensing bars 12 each having a respective plurality of dispensing heads arranged along a respective axis. The plurality of dispensing bars 12 can be fabricated using circuit board or micromachining technologies in materials which include, but are not limited to, polyimide, silicon, glass, and ceramics.

In a preferred embodiment, the plurality of dispensing bars 12 includes a first dispensing bar 14 having a plurality of dispensing heads 16 arranged along an axis 18, a second dispensing bar 20 having a plurality of dispensing heads 22 arranged along an axis 24, a third dispensing bar 26 having a plurality of dispensing heads 28 arranged along an axis 30, and a fourth dispensing bar 32 having a plurality of dispensing heads 34 arranged along an axis 36. It is noted, however, that alternative embodiments can utilize any number of dispensing bars.

Preferably, the plurality of dispensing bars 12 are fixedly positioned relative to one another. As illustrated in FIG. 1, it is preferred that the axes 18, 24, 30, and 36 be parallel to one another. Here, the axes 18, 24, 30, and 36 are offset from one another based upon the spacing between rows of locations on the substrate 10. In particular, the axes 18, 24, 30, and 36 are offset to be simultaneously located over four rows of locations on the substrate 10.

Each plurality of dispensing heads is located colinearly along the axis of its respective dispensing bar. Preferably, each plurality of dispensing heads is fixedly positioned on its dispensing bar. The spacing between adjacent dispensing heads corresponds to the spacing between adjacent locations on the substrate 10. Typically, this spacing is between 100 to 200 μm. Preferably, each of the plurality of dispensing bars 12 covers an entire row of locations on the substrate 10.

Each of the plurality of dispensing bars 12 is operative to selectively deposit a volume of a respective one of a plurality of nucleotide bases in any of a plurality of locations in a respective row on the substrate 10. In the embodiment illustrated in FIG. 1, the first dispensing bar 14 is dedicated for dispensing a first nucleotide type, the second dispensing bar 20 is dedicated for dispensing a second nucleotide type, the third dispensing bar 26 is dedicated for dispensing a third nucleotide type, and the fourth dispensing bar 32 is dedicated for dispensing a fourth nucleotide type. For example, the first nucleotide type can be adenine, the second nucleotide type can be cytosine, the third nucleotide type can be thymine, and the fourth nucleotide type can be guanine to synthesize DNA oligonucleotides. For synthesis of RNA oligonucleotides, the third nucleotide type is uracil rather than thymine.

Each dispensing head is individually controllable for selectively depositing a volume of a single type of nucleotide bases to a location on the substrate 10 below. Although any predetermined volume can be deposited, the volume in oligonucleotide synthesis applications can be in the range of 0.1 nL to 1.0 nL.

Each of the plurality of dispensing bars 12 receives its respective nucleotides from a respective one of a plurality of reservoirs 40 for subsequent deposition on the substrate 10. In particular, the first dispensing bar 14 receives volumes of the first nucleotide type from a first reservoir 42, the second dispensing bar 20 receives volumes of the second nucleotide type from a second reservoir 44, the third dispensing bar 26 receives volumes of the third nucleotide type from a third reservoir 46, and the fourth dispensing bar 32 receives volumes of the fourth nucleotide type from a fourth reservoir 50. In the aforementioned DNA synthesis example, the first reservoir 42 can contain a supply of individual adenine nucleotides, the second reservoir 44 can contain a supply of individual cytosine nucleotides, the third reservoir 46 can contain a supply of individual thymine nucleotides, and the fourth reservoir 50 can contain a supply of individual guanine nucleotides. For RNA synthesis, the third reservoir 46 can contain a supply of individual uracil nucleotides. In order to synthesize oligonucleotides one nucleotide at a time, it is preferred that each nucleotide have a protection group attached at one end using techniques known in the art. Each nucleotide may further include a coupling group attached thereto.

A positioning mechanism 52 positions the substrate 10 with respect to the plurality of dispensing bars 12. In general, the substrate 10 can be positioned with respect to the plurality of dispensing bars 12 by either: (i) repositioning the substrate 10 while the plurality of dispensing bars 12 are fixed; (ii) repositioning the plurality of dispensing bars 12 while the substrate 10 is fixed; or (iii) repositioning both the substrate 10 and the plurality of dispensing bars 12.

In one embodiment, the positioning mechanism 52 includes a translation table or other like conveying apparatus which translates the substrate 10 along an axis 54 transverse to each respective axis of the plurality of dispensing bars 12. In an alternative embodiment, the positioning mechanism 52 translates the plurality of dispensing bars 12 along the axis 54 while the substrate 10 is fixed.

A controller 56 controls the plurality of dispensing bars 12 and the positioning mechanism 52 so that, at each of the plurality of locations, a respective sequence of nucleotide bases is deposited to form a respective oligonucleotide. The controller 56 can include a microprocessor, microcontroller, or other like programmable apparatus which executes a series of programmed steps to control the deposition process. Preferably, the controller 56 is programmable to allow any sequence of nucleotide bases to be deposited at any of the plurality of locations. Here, the system is reconfigurable in software so that the layout of oligonucleotides on the substrate 10 can be readily changed.

A number of control approaches can be utilized to form the plurality of oligonucleotides. In one approach, the controller 56 controls the plurality of dispensing bars 12 and the positioning mechanism 52 to deposit a volume of a single respective nucleotide type at each of the plurality of locations during a single pass of the substrate 10 through the plurality of dispensing bars 12. As a result of the single pass, a layer of nucleotide bases is deposited onto the plurality of locations. If the deposited nucleotide bases have a protection group bound thereto, the protection group is removed prior to a subsequent deposition of nucleotide bases. These steps are repeated for one or more subsequent passes to iteratively build each of the plurality of oligonucleotides.

Figure 2:
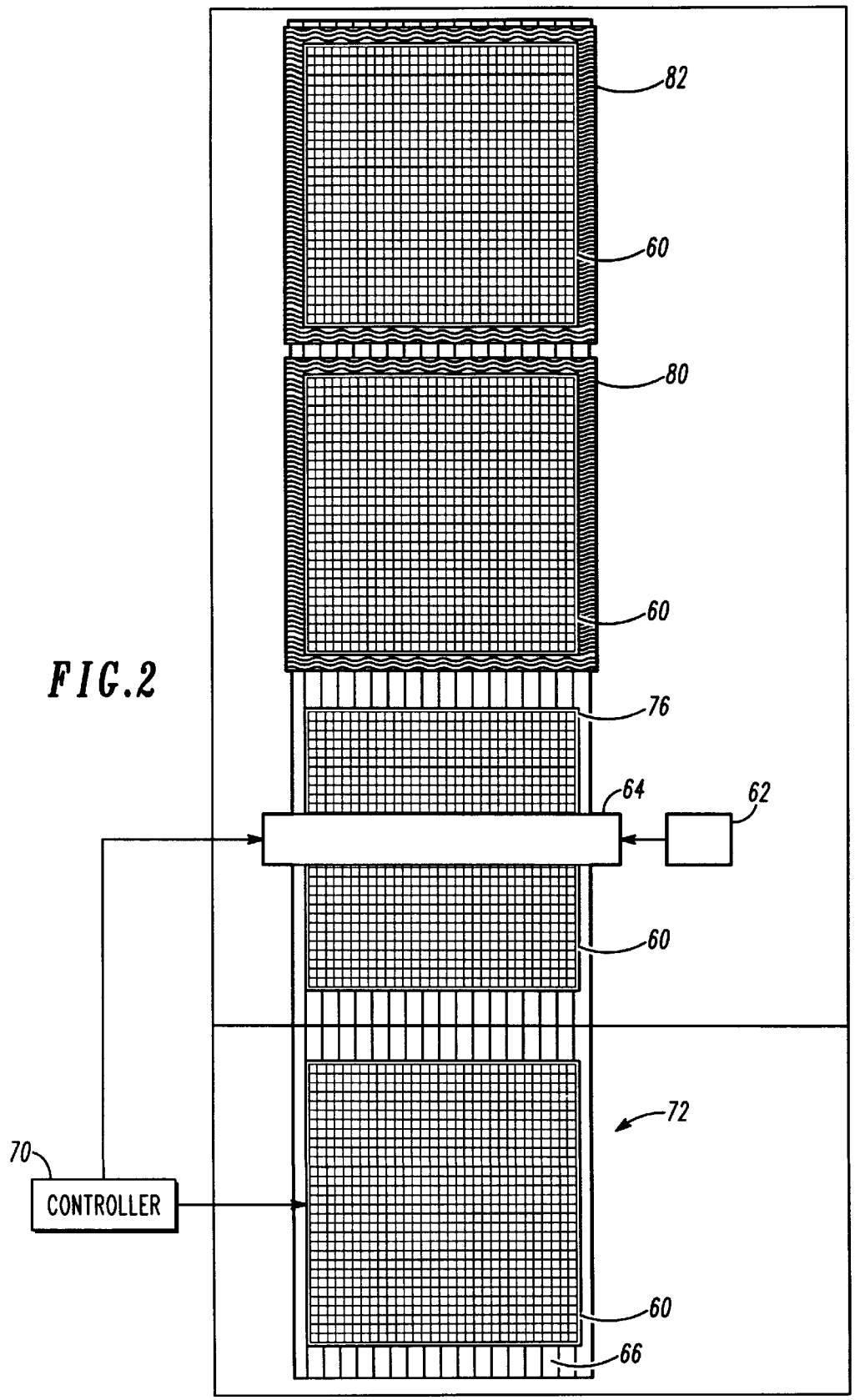
FIG. 2 is an illustration of another embodiment of a system for synthesizing a plurality of oligonucleotides at a plurality of locations on a substrate.

FIG. 2 is an illustration of another embodiment of a system for synthesizing a plurality of oligonucleotides at a plurality of locations on a substrate 60. The system includes a plurality of nucleotide reservoirs 62, a plurality of dispensing bars 64, a positioning mechanism 66, and a controller 70, such as those aforementioned. In this embodiment, the positioning mechanism 66 can take the form of a linear conveyor as illustrated in FIG. 2.

The substrate 60 is initially received at a loading station 72. From the loading station 72, the positioning mechanism 66 transports the substrate 60 to a write station 74 where the plurality of dispensing bars 64 are located. In particular, the positioning mechanism 66 transports the substrate 60 to a position below the plurality of dispensing bars 64. Typically, the substrate 60 is initially positioned so that nucleotides can be deposited at a first end 76 of the substrate 60.

Thereafter, individual dispensing heads in each of the plurality of dispensing bars 64 are addressed to deposit a volume of nucleotide bases to selected locations in at least one row on the substrate 60. Each of these locations, having a respective oligonucleotide sequence which is to be synthesized, receives a corresponding first nucleotide in the respective oligonucleotide sequence.

In embodiments where the plurality of dispensing bars 64 are offset from one another to be located over different rows of locations, volumes of nucleotide bases can be simultaneously deposited on the different rows. For example, four rows can simultaneously receive nucleotide bases in embodiments having four dispensing bars.

The positioning mechanism 66 then repositions the substrate 60 with respect to the plurality of dispensing bars 64 so that subsequent rows of locations can receive their first nucleotide base. Thereafter, the individual dispensing heads in each of the plurality of dispensing bars 64 are again addressed to deposit the first nucleotide base for each respective oligonucleotide sequence in the subsequent rows. The dispensing heads are addressed in a manner such that no nucleotides are deposited on top of nucleotides already deposited during a single pass.

The steps of repositioning the substrate 60 and depositing the nucleotides are repeated until the entire substrate 60 is covered with a predetermined pattern of constituent nucleotides. As a result, each of the locations has a volume of only one type of nucleotide base deposited thereon, namely, the respective first nucleotide base in the oligonucleotide sequence corresponding thereto.

Thereafter, the positioning mechanism 66 transports the substrate 60 to a coupling station 80. The coupling station 80 provides at least one condition which promotes the attachment of a first layer of nucleotides to a surface of the substrate 60. The at least one condition can include providing an appropriate solution which promotes the attachment, and maintaining the substrate 60 in the solution for a predetermined time duration. In one embodiment, the predetermined time duration is a number of minutes.

Once the first layer is attached to the substrate 60, the positioning mechanism 66 transports the substrate to a deprotection device 82. The deprotection device 82 removes the protection group from each respective nucleotide deposited on the substrate 60. Each protection group is removed prior to a subsequent deposition of a subsequent nucleotide at each location, such as would occur in a subsequent pass of the substrate through the plurality of dispensing bars 64. The deprotection device 82 can remove the protection group chemically using various solvents or acids, or photochemically using ultraviolet illumination, for example.

After removing the protection groups, the positioning mechanism 66 transports the substrate 60 back to the write station 74. Here, a subsequent pass of the substrate 60 through the plurality of dispensing bars 64 is performed to deposit a subsequent layer of nucleotides at the plurality of locations. The subsequent layer is deposited in a manner similar to the deposition of the first layer. At each location, a subsequent nucleotide binds to a nucleotide bound to the surface of the substrate 60 to form a nucleotide chain.

The steps of deprotecting and writing can be repeated to synthesize the plurality of oligonucleotides at the plurality of locations. In addition to deprotecting, the deprotection device 82 can apply a capping reagent which caps nucleotide chains which do not react with a deposited nucleotide. This aids in assuring the accuracy of probes synthesized on the substrate 60.

Figure 3:
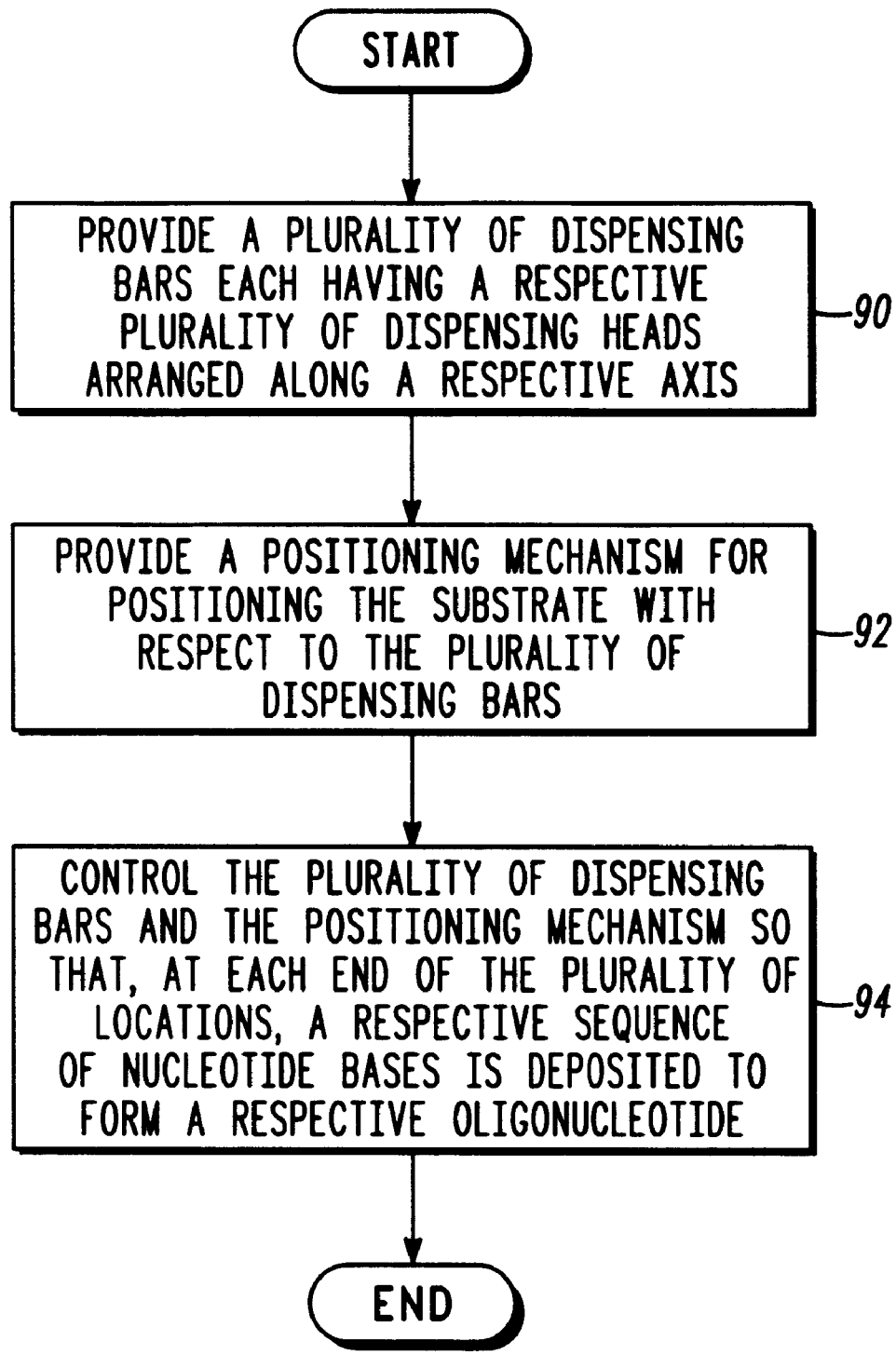
FIG. 3 is a flow chart of a method of synthesizing a plurality of oligonucleotides on a substrate.

FIG. 3 is a flow chart of a method of synthesizing a plurality of oligonucleotides on a substrate. As indicated by block 90, the method includes a step of providing a plurality of dispensing bars each having a respective plurality of dispensing heads arranged along a respective axis. Each of the plurality of dispensing bars is for selectively depositing a volume of a respective one of a plurality of nucleotide bases in any of a plurality of locations along a respective row on the substrate. The plurality of dispensing bars can be provided in accordance with ones described herein.

As indicated by block 92, the method includes a step of providing a positioning mechanism for positioning the substrate with respect to the plurality of dispensing bars. The positioning mechanism can be provided by any of the various positioning mechanisms described herein.

As indicated by block 94, the method includes a step of controlling the plurality of dispensing bars and the positioning mechanism so that, at each of the plurality of locations, a respective sequence of nucleotide bases is deposited to form a respective oligonucleotide.

Figure 4:
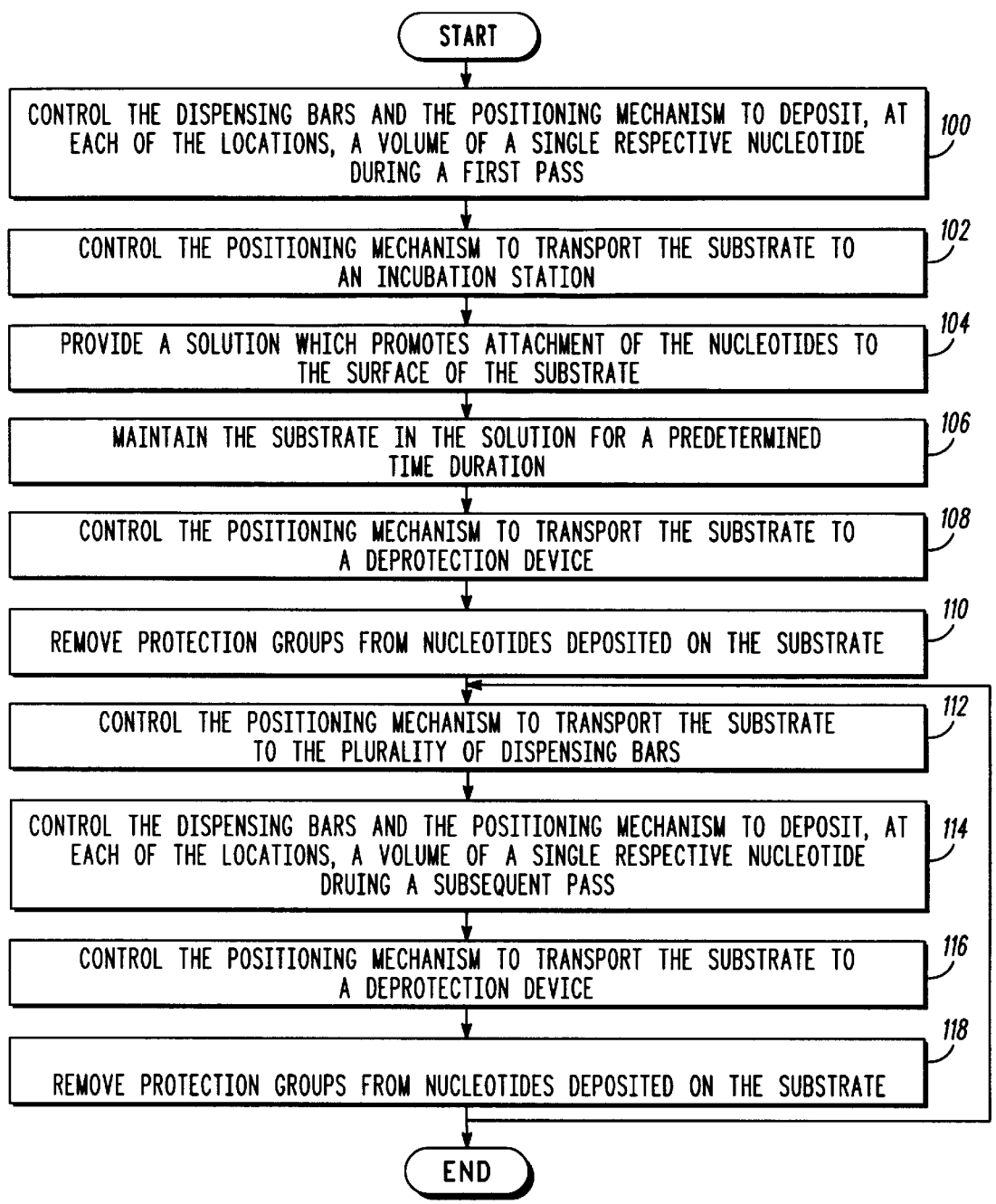
FIG. 4 illustrates a preferred method for controlling the plurality of dispensing bars and the positioning mechanism to form the plurality of oligonucleotides.

FIG. 4 illustrates a preferred method for controlling the plurality of dispensing bars and the positioning mechanism to form the plurality of oligonucleotides. As indicated by block 100, a step of controlling the plurality of dispensing bars and the positioning mechanism is performed to deposit a volume of a single respective nucleotide at each of the locations during a first pass of the substrate through the plurality of dispensing bars. This step forms a first layer of nucleotides on the substrate.

The method further includes steps, indicated by blocks 102, 104, and 106, for providing at least one condition for attaching the first layer of nucleotides to a surface of the substrate. Specifically, block 102 indicates a step of controlling the positioning mechanism to transport the substrate to a coupling station, block 104 indicates a step of providing a solution which promotes attachment of the first layer of nucleotides to the surface, and block 106 indicates a step of maintaining the substrate in the solution for a predetermined time duration.

Once the first layer is attached, a step of controlling the positioning mechanism to transport the substrate to a deprotection device is performed as indicated by block 108. As indicated by block 110, a step of removing the protection group from each respective nucleotide deposited on the substrate is performed prior to a subsequent deposition of a subsequent nucleotide. Here, the protection group is removed at each of the locations prior to a subsequent pass of the substrate through the plurality of dispensing bars.

As indicated by block 112, a step of controlling the positioning mechanism to transport the substrate to the plurality of dispensing bars is performed. As indicated by block 114, a step of controlling the plurality of dispensing bars and the positioning mechanism is performed to deposit a volume of a single respective nucleotide at each of the locations during a subsequent pass of the substrate through the plurality of dispensing bars. This step, similar to the step indicated by block 100, forms a subsequent layer of nucleotides on the substrate.

Thereafter, a step of controlling the positioning mechanism to transport the substrate to a deprotection device is performed as indicated by block 116. Optionally, prior to arriving at the deprotection device, the substrate can be maintained at the coupling station to provide conditions which aid in the coupling of nucleotides to the nucleotide chains. These conditions can include providing an appropriate solution for coupling, waiting a time duration required for coupling, and washing after coupling.

As indicated by block 118, a step of removing the protection group from each respective nucleotide deposited on the substrate in the step of block 114 is performed. Additionally, a capping reagent can be applied to the substrate to cap unreacted nucleotide chains. The steps indicated by blocks 112, 114, 116, and 118 are repeated to synthesize the plurality of oligonucleotides.

It is noted that any of the above-described steps which involve transporting the substrate can include controlling the positioning mechanism to translate the substrate along an axis transverse to each respective axis of the plurality of dispensing bars, or alternatively, to translate the plurality of dispensing bars along an axis transverse to each respective axis of the plurality of dispensing bars.

As described earlier, the methods and steps described herein can be performed with the aid of a controller or other like programmable apparatus. The controller is directed in either software of firmware by computer-readable data stored on a computer-readable storage medium. A computer-readable storage medium having this computer-readable data forms an article of manufacture for directing synthesis of a plurality of oligonucleotides at a plurality of locations on a substrate. The computer-readable storage medium can store the computer-readable data in any of a number of forms which include, but are not limited to, an optical form, an electronic form, and a magnetic form. Hence, the computer-readable storage medium can be embodied by an optical disk, a CD-ROM, a memory, a floppy disk, or a magnetic tape, for example.

Thus, there has been described herein a concept, as well as several embodiments including preferred embodiments of a method and system for synthesizing oligonucleotides using nucleotide-specific dispensing bars.

Because the various embodiments of the present invention utilize a dispensing head for each nucleotide base, they provide a significant improvement in that an array of n-mer probes can be synthesized using n write steps. This compares favorably to the 4 n write steps required to synthesize an array of n-mer probes using lithographic techniques. Further, the problems and expense related to producing and handling lithographic masks are avoided in the various embodiments of the present invention.

Additionally, the various embodiments of the present invention as herein-described allow the layout of oligonucleotides on the substrate to be computer-controlled. As a result, chip layout can be reconfigured in real time in software.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A method of synthesizing a plurality of of oligonucleotides at a plurality of locations on a substrate, the plurality of locations arranged as a plurality of rows on the substrate, the method comprising the steps of:
   (a) providing a plurality of dispensing bars each having a respective plurality of dispensing outlets arranged along a respective axis, each of the plurality of dispensing bars for selectively depositing a volume of a respective one of a plurality of nucleotide bases in any of a plurality of locations along a respective row;
   (b) providing a positioning mechanism for positioning the substrate with respect to the plurality of dispensing bars; and
   (c) controlling the plurality of dispensing bars and the positioning mechanism so that, at each of the plurality of locations, a respective sequence of nucleotide bases is deposited to form a respective oligonucleotide.

2. The method of claim 1 wherein the plurality of dispensing bars includes a first dispensing bar for dispensing a first nucleotide type, a second dispensing bar for dispensing a second nucleotide type, a third dispensing bar for dispensing a third nucleotide type, and a fourth dispensing bar for dispensing a fourth nucleotide type.

3. The method of claim 2 wherein the first nucleotide type contains adenine, the second nucleotide type contains cytosine, the third nucleotide type contains thymine, and the fourth nucleotide type contains guanine.

4. The method of claim 2 wherein the first nucleotide type contains adenine, the second nucleotide type contains cytosine, the third nucleotide type contains uracil, and the fourth nucleotide type contains guanine.

5. The method of claim 1 wherein step (c) includes controlling the positioning mechanism to translate the substrate along an axis transverse to each respective axis of the plurality of dispensing bars.

6. The method of claim 1 wherein step (c) includes controlling the positioning mechanism to translate the plurality of dispensing bars along an axis transverse to each respective axis of the plurality of dispensing bars.

7. The method of claim 1 wherein step (c) includes controlling the plurality of dispensing bars and the positioning mechanism to deposit a volume of a single respective nucleotide at each of the plurality of locations during a single pass of the substrate through the plurality of dispensing bars.

8. The method of claim 7 wherein each single respective nucleotide has a protection group bound thereto, the method further comprising the step of (d) removing the protection group from each respective nucleotide deposited on the substrate prior to a subsequent deposition of a subsequent nucleotide.

9. The method of claim 8 wherein the protection group is removed at each of the plurality of locations prior to a subsequent pass of the substrate through the plurality of dispensing bars.

10. The method of claim 8 wherein step (d) includes controlling the positioning mechanism to transport the substrate to a deprotection device.

11. The method of claim 7 further comprising the step of (d) providing at least one condition for attaching a first layer of nucleotides to a surface of the substrate.

12. The method of claim 11 wherein step (d) includes providing a solution which promotes attachment of the first layer of nucleotides to the surface.

13. The method of claim 12 wherein step (d) includes maintaining the substrate in the solution for a predetermined time duration.

14. The method of claim 11 wherein step (d) includes controlling the positioning mechanism to transport the substrate to a coupling station.

15. The method of claim 1 wherein the plurality dispensing bars are fixedly positioned relative to one another.

16. The method of claim 1 wherein each plurality of dispensing outlets is fixedly positioned on its respective dispensing bar.

17. An article of manufacture for directing synthesis of a plurality of oligonucleotides at a plurality of locations on a substrate, the plurality of locations arranged as a plurality of rows on the substrate, the article of manufacture comprising:
   a computer-readable storage medium; and
   computer-readable data stored on the computer-readable storage medium to direct a controller to control a plurality of dispensing bars, each having a respective plurality of dispensing outlets arranged along a respective axis for selectively depositing a volume of a respective one of a plurality of nucleotide bases in any of a plurality of locations along a respective row of the substrate, and a positioning mechanism for positioning the substrate with respect to the plurality of dispensing bars so that, at each of the plurality of locations, a respective sequence of nucleotide bases is deposited to form a respective oligonucleotide.

18. The article of manufacture of claim 17 wherein the plurality of dispensing bars includes a first dispensing bar for dispensing a first nucleotide type, a second dispensing bar for dispensing a second nucleotide type, a third dispensing bar for dispensing a third nucleotide type, and a fourth dispensing bar for dispensing a fourth nucleotide type.

19. The article of manufacture of claim 18 wherein the first nucleotide type contains adenine, the second nucleotide type contains cytosine, the third nucleotide type contains thymine, and the fourth nucleotide type contains guanine.

20. The article of manufacture of claim 18 wherein the first nucleotide type contains adenine, the second nucleotide type contains cytosine, the third nucleotide type contains uracil, and the fourth nucleotide type contains guanine.

21. The article of manufacture of claim 17 wherein the computer-readable data directs the controller to control the positioning mechanism to translate the substrate along an axis transverse to each respective axis of the plurality of dispensing bars.

22. The article of manufacture of claim 17 wherein the computer-readable data directs the controller to control the positioning mechanism to translate the plurality of dispensing bars along an axis transverse to each respective axis of the plurality of dispensing bars.

23. The article of manufacture of claim 17 wherein the computer-readable data directs the controller to control the plurality of dispensing bars and the positioning mechanism to deposit a volume of a single respective nucleotide at each of the plurality of locations during a single pass of the substrate through the plurality of dispensing bars.

24. The article of manufacture of claim 23 wherein each single respective nucleotide has a protection group bound thereto, wherein the computer-readable data directs a removing of the protection group from each respective nucleotide deposited on the substrate prior to a subsequent deposition of a subsequent nucleotide.

25. The article of manufacture of claim 24 wherein the protection group is removed at each of the plurality of locations prior to a subsequent pass of the substrate through the plurality of dispensing bars.

26. The article of manufacture of claim 24 wherein the computer-readable data directs the controller to control the positioning mechanism to transport the substrate to a deprotection device.

27. The article of manufacture of claim 23 wherein the computer-readable data directs at least one condition for attaching a first layer of nucleotides to a surface of the substrate.

28. The article of manufacture of claim 27 wherein the computer-readable data directs a solution to be provided to the substrate, the solution for promoting attachment of the first layer of nucleotides to the surface.

29. The article of manufacture of claim 28 wherein the computer-readable data directs the substrate to be maintained in the solution for a predetermined time duration.

30. The article of manufacture of claim 27 wherein the computer-readable data directs the controller to control the positioning mechanism to transport the substrate to a coupling station.

31. The article of manufacture of claim 17 wherein the plurality of dispensing bars are fixedly positioned relative to one another.

32. The article of manufacture of claim 17 wherein each plurality of dispensing outlets is fixedly positioned on its respective dispensing bar.

* * * * *